US005601845A

United States Patent [19]
Buxton et al.

[11] Patent Number: 5,601,845
[45] Date of Patent: Feb. 11, 1997

[54] PHARMACEUTICAL SPHEROID FORMULATION

[75] Inventors: Ian R. Buxton; Helen Critchley; Stewart T. Leslie; Derek A. Prater, all of Cambridge, United Kingdom; Ronald B. Miller, Basle, Switzerland; Sandra T. A. Malkowska, Cambridge, United Kingdom

[73] Assignee: Euro-Celtique, S.A., Luxembourg

[21] Appl. No.: 666,636

[22] Filed: Jun. 18, 1996

Related U.S. Application Data

[63] Continuation of Ser. No. 425,888, Apr. 21, 1995, abandoned, which is a continuation of Ser. No. 926,501, Aug. 5, 1992, abandoned.

[30] Foreign Application Priority Data

Aug. 12, 1991 [GB] United Kingdom .................... 9117361
Oct. 29, 1991 [GB] United Kingdom .................... 9122967

[51] Int. Cl.$^6$ ............................. A61K 9/16; A61K 9/62; A61K 9/26
[52] U.S. Cl. ........................ 424/495; 424/461; 424/469
[58] Field of Search ................................... 424/495, 499, 424/470, 461, 462, 469; 514/781, 951

[56] References Cited

U.S. PATENT DOCUMENTS

| | | | |
|---|---|---|---|
| 4,456,628 | 6/1984 | Bauer et al. | 424/495 |
| 4,721,619 | 1/1988 | Panoz et al. | 424/459 |
| 4,808,413 | 2/1989 | Joshi | 424/458 |
| 4,894,240 | 1/1990 | Geoghegan et al. | 424/497 |
| 4,917,899 | 4/1990 | Geoghegan et al. | 424/461 |
| 4,917,900 | 4/1990 | Jones et al. | 424/493 |
| 4,960,596 | 10/1990 | Debregeas et al. | 424/458 |
| 5,002,776 | 3/1991 | Geoghegan et al. | 424/497 |
| 5,112,621 | 5/1992 | Stevens et al. | 424/497 |
| 5,219,621 | 6/1993 | Geoghegan et al. | 424/462 |
| 5,286,497 | 2/1994 | Hendrickson et al. | 424/490 |
| 5,364,620 | 11/1994 | Geoghegan et al. | 424/462 |

FOREIGN PATENT DOCUMENTS

| | | | |
|---|---|---|---|
| 615221 | 6/1989 | Australia | A61K 9/24 |
| 3227389 | 10/1989 | Australia . | |
| 6798890 | 7/1991 | Australia . | |
| 634660 | 9/1991 | Australia | A61K 31/55 |
| 1327006 | 2/1994 | Canada | A61K 31/55 |
| 0149920 | 7/1985 | European Pat. Off. | A61K 31/55 |
| 0154009 | 9/1985 | European Pat. Off. | A61K 31/54 |
| 0288732 | 11/1988 | European Pat. Off. . | |
| 0351414 | 5/1989 | European Pat. Off. . | |
| 0315414 | 5/1989 | European Pat. Off. . | |
| 0317855 | 5/1989 | European Pat. Off. | A61K 31/54 |
| 0322277 | 6/1989 | European Pat. Off. . | |
| 0320097 | 6/1989 | European Pat. Off. | A61K 31/55 |
| 0373417 | 6/1990 | European Pat. Off. | A61K 9/20 |
| 0163000 | 4/1991 | European Pat. Off. | A61K 9/52 |
| 0106443 | 7/1991 | European Pat. Off. | A61K 9/22 |
| 0446753 | 9/1991 | European Pat. Off. . | |
| 0514814 | 11/1992 | European Pat. Off. | A61K 31/55 |
| 0220670 | 1/1993 | European Pat. Off. | A61K 9/54 |
| 56999 | 3/1992 | Ireland | A61K 9/52 |
| 662507 | 10/1987 | Switzerland | A61K 31/38 |
| 2179251 | 8/1989 | United Kingdom | A61M 31/00 |
| 2227172 | 7/1990 | United Kingdom | A61K 31/55 |
| 2209280 | 9/1991 | United Kingdom | A61K 9/52 |
| 8802253 | 4/1988 | WIPO . | |
| 8908448 | 9/1989 | WIPO | A61K 9/52 |
| 9101722 | 2/1991 | WIPO . | |

OTHER PUBLICATIONS (Abstract), *Pharmaceuticals*, p. 8, Week K23, Abstract #54403 K/23 (EP–80–341), "Pharmaceutical multiple units formulation – with enterically coated cores for reduced peak plasma drug concentration", Benzon A AS.

(Abstract) *Pharmaceuticals*, Week K25, Abstract #59112 K/25 (EP–81–006), "Composition of beta–adrenergic blocer and tetra–hydro–benzazepine – useful as atihypertensive and in improving efficiency of kidney function", Alcide Co. Ltd. Partn (ALLI).

(Abstract) *Pharmaceuticals*, p. 3, Week 8407, Abstract #84–038350/07 (EP–100–061–A), "Pharmaceutical dosage units with enhanced bio:availability – especially hydro:chloro:thiazide–triamterene mixtures for uniform absoprtion", Mylan Pharm, Inc.

(Abstract) *Pharmaceuticals*, p. 6, Week 8528, Abstract #85–166500/28 (EP–147–750–A), "Pharmaceutical composition for oral, rectal or vaginal administration – with polyvinyl alcohol film coating for controlled and prolonged release", (Merck & Co., Inc.

(Abstract) No. 22342C/13 (EP–9–657), "Diuretic compositions containing potassium retaining agents – comprising 2,4–di:amino–5–aminobenzyl–pyrimidine derivatives", Hoffman–LaRoche AG.

(Abstract) No. 1593062, "Pharmaceutical controlled release compositions", 16 Sep. 1977, Richter Gedeon Vegyeszeti Gyar RT.

(Abstract), No. 85–184021/31 (EP–154–009–A), "Treatment of hypertension in patent – by administration of thiazide diuretic at level to cause antihypertensive action with diuresia", Euro–Celtique, S.A.

(Abstract), No. 89–158961/22 (EP–317–855–A), "Combination of moxonidine, hydro:chloro:thiazide and opt. triamteren – for long–term treatment of hypertonia and oedemas", Beiersdorf AG.

*Primary Examiner*—Edward J. Webman
*Attorney, Agent, or Firm*—Steinberg, Raskin & Davidson, P.C.

[57] ABSTRACT

A controlled release composition including spheroid cores of diltiazem. or a pharmaceutically acceptable salt thereof and optionally a spheronizing agent, the cores being coated with a controlled release layer, and a method of manufacturing the same, is disclosed. The spheronizing agent when present is preferably microcrystalline cellulose. Ethylcellulose is a preferred release coating. The controlled release coating preferably contains a plasticizer, a surfactant and a tack-modifier.

17 Claims, No Drawings

PHARMACEUTICAL SPHEROID FORMULATION

This is a continuation of application Ser. No. 08/425,888, filed Apr. 21, 1995, now abandoned, which is incorporated by reference herein in its entirety, and which is a continuation of Ser. No. 07/926,501, filed Aug. 5, 1992, now abandoned.

BACKGROUND OF THE INVENTION

The present invention relates to a controlled release preparation and to a process for its preparation. In particular it relates to a controlled release preparation containing diltiazem.

Diltiazem is a calcium antagonist which has been shown to be useful in treating chronic heart disease such as hypertension and angina.

OBJECTS AND SUMMARY OF THE INVENTION

It is an object of the present invention to provide a controlled release diltiazem preparation suitable for once daily administration for the treatment of hypertension and angina.

In view of the above object and others, the present invention is related to a controlled release composition comprising spheroid cores comprising diltiazem or a pharmaceutically acceptable salt thereof in an amount effective to render a therapeutic effect, and optionally a spheronizing agent, the cores being coated with a controlled release material in an amount effective to provide a controlled release of diltiazem when said composition is exposed to aqueous solutions.

In certain preferred embodiments of the present invention, the controlled release layer is provided in an amount suitable to provide a once daily dosage regimen.

The present invention is also related to a process for preparing a controlled release oral dosage preparation of diltiazem, comprising (a) granulating a mixture comprising diltiazem or a pharmaceutically acceptable salt thereof with water and optionally a spheronizing agent; (b) extruding the granulated mixture to obtain an extrudate; (c) spheronizing the extrudate until spheroid cores are formed; (d) drying the spheroid cores; and (e) coating the spheroid cores with a controlled release material. Thereafter, the coated spheroid cores are filled into capsules or sachets or compressed into tablets in an amount effective to provide a therapeutic dosage of diltiazem when ingested orally by a patient.

In a preferred embodiment of the present invention, the resultant controlled release formulation of diltiazem is a one-a-day dosage.

DETAILED DESCRIPTION

Diltiazem is a calcium antagonist (calcium channel blocker) commonly available as the hydrochloride salt and having the chemical name 1,5-Benzothiazepin-4(5H)one,3-(acetyloxy)-5-[2-(dimethylamino)-et hyl]-2,3-dihydro-2-(4-methoxyphenyl)-, monohydrochloride, (+)-cis-.

Suitable pharmaceutically acceptable salts of diltiazem for use according to the present invention include pharmaceutically acceptable acid addition salts. The hydrochloride salt is particularly preferred.

A controlled release pharmaceutical composition according to the present invention is one that achieves slow release of a drug over an extended period of time and extends the duration of drug action over that achieved by conventional delivery.

The term "spheroid" is conventional in the pharmaceutical art and means a spherical granule having a diameter of between 0.1 mm and 2.5 mm, especially between 0.5 mm and 2 mm.

The spheroid cores for use according to the present invention preferably contain from about 40% to about 98%, more preferably from about 60% to about 85%, and most preferably from about 70% to about 85% by weight of diltiazem or its pharmaceutically acceptable salts.

The spheronizing agent may comprise any pharmaceutically acceptable material which may be spheronized together with the active ingredient to form spheroid cores. A preferred spheronizing agent is microcrystalline cellulose. The microcrystalline cellulose employed may be, for example, Avicel PH 101 or Avicel PH 102 (mFMC Corporation). Conveniently the spheronizing agent, when present, is present in an amount of from 1% to 60%, and preferably from 15% to 40%, by weight of the spheroid cores.

Optionally, the spheroid cores may also contain other pharmaceutically acceptable excipients and diluents which facilitate spheronization such as pharmaceutically acceptable sugars (for example sucrose, dextrose, maltose or lactose) or pharmaceutically acceptable sugar alcohols (for example mannitol, xylitol or sorbitol). Colorants may also be included in the spheroid core.

The spheroid cores are coated with a material which permits release of the diltiazem at a controlled rate in an aqueous medium. Suitable controlled release coating materials. include those well known in the art such as water insoluble waxes and polymers such as polymethacrylates (for example, Eudragit polymers™) or, preferably, water insoluble celluloses (for example, alkylcelluloses such as ethylcellulose). The coating may also include water soluble polymers such as polyvinylpyrrolidone or, preferably, a water soluble cellulose such as hydroxypropylmethylcellulose and/or hydroxypropylcellulose. It will be appreciated that the ratio of water insoluble to water soluble material will depend on the release rate required and the solubility of the materials selected. The ratio of water soluble polymer to water insoluble polymer is preferably from about 1:20 to about 1:2.

The controlled release coating preferably includes one or more pharmaceutically acceptable plasticizers conventional in the art such as diethylphthalate, or, preferably, dibutyl sebacate; surfactants such as sorbitan trioleate, sorbitan monolaurate, or, preferably, polysorbate 80 (Tween 80™); and tack-modifiers, such as talc, or, preferably, colloidal anhydrous silica.

The amount of plasticizer, when present, will depend on the particular plasticizer selected. In general, the plasticizer is present in an amount from about 1% to about 25% by weight of the controlled release film coat. The surfactant, when present, is suitably present in an amount from about 1% to about 25% by weight of the controlled release film coat. The tack-modifier, when present, is also suitably present in an amount from about 1% to about 25% by weight of the controlled release film coat.

A preferred controlled release film coating in accordance with the present invention comprises from about 50% to about 95% ethylcellulose, from about 5% to about 15% colloidal anhydrous silica, from about 5% to about 15% dibutyl sebacate, and from about 5% to about 15% polysorbate 80 (Tween 80™).

The controlled release film coating layer can be formed on the surface of the diltiazem-containing spheroid cores using conventional coating methods, for example fluidized bed or pan coating. The coating materials may be applied as a solution or suspension. Suitable solvent systems include water, dichloromethane, ethanol, methanol, isopropyl alcohol and acetone mixtures thereof, and the like. The coating solution or suspension preferably contains from about 2% to about 60%, and preferably from about 2% to about 20% by weight of coating materials.

The amount of the controlled release coating material applied onto the spheroid cores will depend on the desired release rate. Generally, the amount of the controlled release coating material in the formulation is in the range of from about 1% to about 25%, and preferably from about 2% to about 8%, by weight of the composition.

The controlled release composition according to the invention may be prepared by
(a) granulating a mixture comprising diltiazem or a pharmaceutically acceptable salt thereof, water and optionally a spheronizing agent;
(b) extruding the granulating mixture to give an extrudate;
(c) spheronizing the extrudate until spheroid cores are formed; and
(d) film-coating the spheroid cores with a controlled release coating.

Compositions according to the invention may be filled into capsules or sachets or compressed into tablets using conventional pharmaceutical techniques.

In a preferred embodiment, the composition according to the present invention may be orally administered once daily. Conveniently, for once daily administration the dosage form contains from 120 mg to 300 mg to diltiazem or a pharmaceutically acceptable salt thereof, preferably diltiazem hydrochloride.

DETAILED DESCRIPTION OF THE PREFERRED EMBODIMENTS

The following examples illustrate various aspects of the present invention. They are not to be construed to limit the claims in any manner whatsoever.

EXAMPLE 1

In Example 1, diltiazem capsules were prepared in accordance with the present invention. First, diltiazem hydrochloride and microcrystalline cellulose were blended using a high shear mixer. The mixture was wet granulated, and extruded to give an extrudate which was spheronized and dried in a fluid bed drier. The spheroids were sieved to give a particle size of 0.85 to 1.7 mm. The diltiazem spheres had the composition set forth in Table 1 below:

TABLE 1

| Diltiazem Spheroid Cores | |
| --- | --- |
| Material | mg |
| Diltiazem hydrochloride U.S.P. | 120 |
| Microcrystalline cellulose E.P. (Avicel PH101) | 30.0 |
| Purified water E.P. | q.s. |
| Total | 150 |

The controlled release film coating ingredients, ethylcellulose, colloidal anhydrous silica, dibutyl sebacate, and polysorbate 80, were dispersed in a dichloromethane/methanol solvent system. The amounts of the above materials used to prepare the coating are set forth in Table 2 below:

TABLE 2

| Controlled Release Film Coat | |
| --- | --- |
| Material | mg |
| Diltiazem hydrochloride spheroid core | 150 |
| Ethylcellulose N10 U.S.N.F. | 7.38 |
| Colloidal anhydrous silica E.P. (Aerosil 130) | 0.988 |
| Dibutyl sebacate U.S.N.F. | 0.742 |
| Polysorbate 80 E.P. (Tween 80) | 0.791 |
| Dichloromethane BS 1994 | q.s. |
| Methanol B.P. 1973 | q.s. |
| Total | 160 |

The controlled release film coat was then applied to the diltiazem spheroid cores in a fluid bed coater. The resulting film coated spheroids were sieved. The coated spheroids were filled into gelatin capsule shells. Further information is provided in Table 3 below:

TABLE 3

| Capsule formulation | |
| --- | --- |
| Material | mg |
| Diltiazem controlled release spheroids | 160 |
| Magnesium stearate E.P. | 0.480 |
| Gelatin capsule shells size 3 | |

The resulting capsule were thereafter subjected to dissolution testing measured by E.P. basket apparatus at 100 rpm in a pH 4.5 E.P. phosphate buffer. The results obtained are recorded in Table 4 below:

TABLE 4

| Diltiazem Dissolution | |
| --- | --- |
| Time (hours) | Percent Diltiazem Released |
| 1 | 9 |
| 2 | 23 |
| 3 | 37 |
| 4 | 48 |
| 5 | 57 |
| 6 | 63 |
| 8 | 72 |
| 10 | 77 |
| 12 | 81 |
| 15 | 86 |
| 20 | 90 |

The examples provided above are not meant to be exclusive. Many other variations of the present invention would be obvious to those skilled in the art, and are contemplated to be within the scope of the appended claims.

What is claimed is:

1. A solid, controlled release oral diltiazem formulation providing a one day dosage of diltiazem comprising
spheroid cores consisting of from about 60% to about 85% diltiazem or a pharmaceutically acceptable salt thereof and from about 15% to about 40% by weight of a spheronizing agent consisting of microcrystalline cellulose, said spheroid cores being in a sufficient amount to render a therapeutic effect over a one day period, said spheroid cores being coated with from about 1% to about 25% by weight of a controlled release material comprising ethyl cellulose in an amount effective to provide controlled release diltiazem over a one day period when said composition is exposed to aqueous solutions.

2. The formulation according to claim 1, wherein the coated spheroid cores are contained within a capsule.

3. The formulation according to claim 20 wherein the capsule contains an amount of diltiazem ranging from about 120 to about 300 mg of diltiazem or a pharmaceutically acceptable salt thereof.

4. The capsule according to claim 2 comprising about 160 mg of the diltiazem controlled release spheroids.

5. The formulation according to claim 1, wherein the coated spheroid cores are compressed into a tablet.

6. The formulation according to claim 5 wherein the diltiazem is present in an amount ranging of from about 120 to about 300 mg of diltiazem or a pharmaceutically acceptable salt thereof.

7. The formulation according to claim 6 wherein the diltiazem is present in an amount consisting of about 120 mg of diltiazem hydrochloride.

8. The formulation according to claim 6 wherein the diltiazem is present in an amount consisting of about 150 mg of diltiazem hydrochloride.

9. The formulation according to claim 1 wherein the diltiazem is present in an amount ranging from about 70% to about 85% by weight of the spheroid cores.

10. The formulation according to claim 1 wherein the controlled release coating material further comprises an excipient selected from the group consisting of a plasticizer, a surfactant, a tack-modifier and a mixture of any of the forgoing.

11. The formulation according to claim 10 wherein the plasticizer is diethylphthalate.

12. The formulation according to claim 10 wherein the plasticizer is dibutyl sebacate.

13. The formulation according to claim 10 wherein the surfactant is sorbitan trioleate.

14. The formulation according to claim 10 wherein the surfactant is sorbitan monolaurate.

15. The formulation according to claim 10 wherein the surfactant is polysorbate 80.

16. The formulation according to claim 10 wherein the tack modifier is present in an amount ranging from about 1% to about 25% by weight of the controlled release coating material.

17. The formulation according to claim 1 wherein the controlled release coating material is present in an amount of from about 2% to about 8% by weight of the composition.

* * * * *